United States Patent
Miller et al.

(10) Patent No.: US 12,324,664 B2
(45) Date of Patent: Jun. 10, 2025

(54) MICROVOLUME 3-WAY STOPCOCK AND METHOD FOR OBTAINING CLEAN BLOOD SPECIMEN

(71) Applicant: UTAH MEDICAL PRODUCTS, INC., Midvale, UT (US)

(72) Inventors: Jonathan K. Miller, Farmington, UT (US); Ben D. Shirley, Draper, UT (US)

(73) Assignee: UTAH MEDICAL PRODUCTS, INC., Midvale, UT (US)

( * ) Notice: Subject to any disclaimer, the term of this patent is extended or adjusted under 35 U.S.C. 154(b) by 665 days.

(21) Appl. No.: 17/686,369

(22) Filed: Mar. 3, 2022

(65) Prior Publication Data
US 2023/0277102 A1    Sep. 7, 2023

(51) Int. Cl.
*A61B 5/15* (2006.01)
*A61M 39/22* (2006.01)

(52) U.S. Cl.
CPC .. *A61B 5/150221* (2013.01); *A61B 5/150213* (2013.01); *A61B 5/150992* (2013.01); *A61M 39/223* (2013.01); *A61M 2039/229* (2013.01)

(58) Field of Classification Search
CPC ........ A61B 5/150221; A61B 5/150213; A61B 5/150992; A61B 5/150251; A61B 5/15003; A61B 5/153; A61B 5/155; A61M 39/223; A61M 2039/229
See application file for complete search history.

(56) References Cited

U.S. PATENT DOCUMENTS

| | | | |
|---|---|---|---|
| 4,024,857 A | | 5/1977 | Blecher et al. |
| 4,447,235 A | * | 5/1984 | Clarke ............. A61M 25/0606 600/573 |
| 4,763,648 A | | 8/1988 | Wyatt |
| 5,893,834 A | | 4/1999 | Duchamp |
| 5,916,202 A | | 6/1999 | Haswell |
| 6,156,019 A | * | 12/2000 | Langevin ............... A61B 5/412 604/323 |
| 6,217,556 B1 | * | 4/2001 | Ellingson ........... A61B 10/0283 604/167.03 |

(Continued)

OTHER PUBLICATIONS

Ameritus Medical Products, Hummi Closed Needleless Micro-Draw Blood Transfer Device, PSS-HUMMI rev6-13, 2012.

*Primary Examiner* — Charles A Marmor, II
*Assistant Examiner* — Severo Antonio P Lopez
(74) *Attorney, Agent, or Firm* — KIRTON McCONKIE; Evan R. Witt

(57) ABSTRACT

A microvolume 3-way stopcock for use in a blood sampling system. The stopcock includes a stopcock body having a cylindrical-shaped central chamber, an inlet fluid passage extending from the central chamber to a connector, a blood sample fluid passage extending from the central chamber to a connector, and a waste fluid passage extending from the central chamber to a connector. A rotatable flow control member having a T-shaped fluid passage is disposed within the central chamber. The rotatable flow control member provides adjustable fluid communication between the inlet, blood sample, and/or waste fluid passages. The stopcock is configured with a small dead space volume in the range from about 0.02 mL to 0.20 mL. A cannula may be connected to the inlet fluid passage. The combined dead space fluid volume of the stopcock and cannula may range from about 0.03 ml to 0.24 mL.

19 Claims, 7 Drawing Sheets

(56) References Cited

U.S. PATENT DOCUMENTS

| | | |
|---|---|---|
| 6,416,510 B1* | 7/2002 | Altman .............. A61B 18/1492 606/41 |
| 8,096,958 B2 | 1/2012 | Sarstedt |
| 8,152,786 B2 | 4/2012 | Shapland et al. |
| 10,980,462 B2 | 4/2021 | Cash |
| 2016/0213911 A1* | 7/2016 | Liu ....................... F16K 11/072 |
| 2018/0207398 A1* | 7/2018 | Jho ....................... A61M 39/02 |
| 2019/0275312 A1* | 9/2019 | Chelak .................. A61M 25/02 |

* cited by examiner

MICROVOLUME 3-WAY STOPCOCK AND METHOD FOR OBTAINING CLEAN BLOOD SPECIMEN

FIELD OF THE INVENTION

Embodiments of the present disclosure generally relate to medical devices and methods for obtaining a clean blood specimen. More particularly, the present disclosure relates to a microvolume 3-way stopcock for neonatal blood sampling which significantly reduces the fluid-path dead space. The invention also relates to a method for obtaining a clean blood specimen utilizing the 3-way stopcock.

BACKGROUND OF THE INVENTION

Obtaining patient blood specimens is a common procedure in modern medical care. However, special care must be taken when obtaining blood specimens from neonatal patients due to their low total blood volume. A larger acute loss of blood volume may compromise the patient's circulation or otherwise harm the patient. Guidelines for blood specimen volume limits range from about 1% to 5% of total blood volume within 24 hours. Thus, very small blood volumes may be safely obtained from neonatal patients.

Devices used to obtain blood specimens contain a dead space volume which must be filled with blood before the actual blood specimen can be obtained. Thus, to obtain a clean blood specimen, sufficient blood must be drawn into the sampling apparatus to clear the dead space volume.

It would be an advancement in the art to provide an apparatus and method for obtaining blood specimens which require a low dead space fluid volume to be cleared before obtaining a blood specimen. It would be an advancement in the art to provide an apparatus for obtaining blood specimens having a low dead space fluid volume.

BRIEF SUMMARY OF THE INVENTION

Implementation of the present disclosure provides a blood sampling system and methods for obtaining a clean blood specimen utilizing the blood sampling system. The disclosed blood sampling system includes a microvolume 3-way stopcock. As used herein, the term "microvolume 3-way stopcock" is a 3-way stopcock designed to allow a medical professional to obtain a desired volume of clean blood specimen, which may be a fraction of 1 mL, while wasting a "microvolume" of patient blood during the process due to dead space in the device and requiring a significantly reduced flush volume to clear blood out of the line after each blood draw. As used herein, the term "dead space" refers to the internal fluid volume of the 3-way stopcock which must be filled with blood before blood can flow into a blood specimen collection device. Various embodiments are described herein. It will be understood that the embodiments listed below may be combined not only as listed below, but in other suitable combinations in accordance with the scope of the invention.

The stopcock includes a stopcock body. In one or more disclosed embodiments, the stopcock body comprises a cylindrical-shaped central chamber, an inlet fluid passage extending from the central chamber to a male luer connector, a blood sample fluid passage extending from the central chamber to a female luer connector, and a waste fluid passage extending from the central chamber to a female luer connector.

In one or more disclosed embodiments, a rotatable flow control member is disposed within the central chamber. The rotatable flow control member may comprise an internal T-shaped fluid passage. The rotatable flow control member provides adjustable fluid communication between the inlet fluid passage, the blood sample fluid passage, and/or the waste fluid passage.

In one or more disclosed embodiments, a lever connected to the rotatable flow control member permits selective rotation of the rotatable flow control member which controls fluid flow between the fluid passages.

In one or more disclosed embodiments, the inlet, blood sample, waste, and T-shaped fluid passages have an inner cross-sectional area in the range from 0.3 to 2.0 square millimeters, e.g., 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 square millimeters, where any of the stated values can form an upper or lower endpoint of a range. The inner cross-sectional area may take any practical shape, including, but not limited to, circular, oval, polygonal, etc.

In one or more disclosed embodiments, the microvolume 3-way stopcock has a fluid volume dead space in the range of 0.02 to 0.10 mL. In one or more disclosed embodiments, the microvolume 3-way stopcock has a fluid volume dead space in the range of 0.02 to 0.15 mL. In one or more disclosed embodiments, the microvolume 3-way stopcock has a fluid volume dead space in the range of 0.02 to 0.20 mL. The microvolume 3-way stopcock may have a fluid volume dead space of 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, or 0.20 mL, where any of the stated values can form an upper or lower endpoint of a range.

In one non-limiting embodiment, the inlet fluid passage comprises a cannula insert disposed within the inlet fluid passage.

In one or more disclosed embodiments, the blood sample fluid passage comprises a blood sample cone disposed within the blood sample fluid passage.

In one or more disclosed embodiments, the waste fluid passage comprises a waste cone disposed within the waste fluid passage.

In one or more disclosed embodiments, the cannula insert, the blood sample cone, and the waste cone comprise lengthwise fluid pathways have an inner cross-sectional area in the range from 0.3 to 2.0 square millimeters, e.g., 0.3, 0.4, 0.5, 0.6, 0.7, 0.8, 0.9, 1.0, 1.1, 1.2, 1.3, 1.4, 1.5, 1.6, 1.7, 1.8, 1.9, or 2.0 square millimeters, where any of the stated values can form an upper or lower endpoint of a range. The inner cross-sectional area may take any practical shape, including, but not limited to, circular, oval, polygonal, etc.

The disclosed blood sampling system may further include a cannula connected to the male luer connector.

The disclosed blood sampling system may further include a self-venting blood sample syringe connected to the female luer connector of the blood sample fluid passage.

The disclosed blood sampling system may further include a self-venting waste syringe connected to the female luer connector of the waste fluid passage.

The disclosed invention further relates to a method for obtaining a clean blood specimen. In one or more disclosed embodiments of the method the blood specimen is obtained from an arterial line. Non-limiting examples of an arterial line include an indwelling umbilical arterial catheter (UAC) and a peripheral arterial line (PAL). In the method, a sterile septum connector is connected to the arterial line. The sterile septum connector may be connected to the arterial line by a clinician obtaining the blood specimen. If a septum connection is already connected to the arterial line, then the clinician may prepare and sterilize the septum connector. The septum connector provides a closed system access point.

The method for obtaining a clean blood specimen uses a microvolume 3-way stopcock. In one or more disclosed embodiments, the 3-way stopcock comprises an inlet fluid passage having a male luer connector and a cannula attached to the male luer connector, a blood sample fluid passage having a female luer connector, and a waste fluid passage having a female luer connector.

In one or more disclosed embodiments, a rotatable flow control member is configured to provide adjustable fluid communication between the inlet fluid passage, the blood sample fluid passage, and/or the waste fluid passage.

In one or more disclosed embodiments, the microvolume 3-way stopcock and cannula have a combined dead space fluid volume in the range from 0.03 to 0.14 mL. In one or more disclosed embodiments, the microvolume 3-way stopcock and cannula have a combined dead space fluid volume in the range from 0.03 to 0.19 mL. In one or more disclosed embodiments, the microvolume 3-way stopcock and cannula have a combined dead space fluid volume in the range from 0.03 to 0.24 mL. The microvolume 3-way stopcock and cannula may have a combined dead space fluid volume of 0.03, 0.04, 0.05, 0.06, 0.07, 0.08, 0.09, 0.10, 0.11, 0.12, 0.13, 0.14, 0.15, 0.16, 0.17, 0.18, 0.19, 0.20, 0.21, 0.22, 0.23, or 0.24 mL, where any of the stated values can form an upper or lower endpoint of a range.

In one or more disclosed embodiments of the method, a self-venting first blood sample syringe is connected to the female luer connector of the blood sample fluid passage and a self-venting waste syringe is connected to the female luer connector of the waste fluid passage.

The flow control member is rotated to close fluid flow from the cannula and the inlet fluid passage. The cannula is inserted into the septum connector.

The flow control member is rotated to permit fluid flow between the inlet fluid passage and the waste fluid passage and to allow waste blood into the waste syringe.

The flow control member is rotated to permit fluid flow between the inlet fluid passage and the blood sample fluid passage and to allow a desired first blood sample into the first blood sample syringe.

The flow control member is rotated to permit fluid flow between the inlet fluid passage and the waste fluid passage.

The waste blood is returned from the waste syringe to the patient.

In one or more disclosed embodiments of the disclosed method for obtaining a clean blood specimen, the flow control member is rotated to close fluid flow from the arterial line. The cannula is removed from the septum connector. The first blood sample syringe is removed from the female luer connector of the blood sample fluid passage.

In one or more disclosed embodiments of the disclosed method for obtaining a clean blood specimen, the arterial line is an indwelling umbilical catheter or a peripheral arterial line.

In one or more disclosed embodiments of the disclosed method for obtaining a clean blood specimen, after the self-venting first blood sample syringe is connected to the female luer connector of the blood sample fluid passage, the self-venting first blood sample syringe is set to a desired blood sample volume.

In one or more disclosed embodiments of the disclosed method for obtaining a clean blood specimen, after the self-venting waste syringe is connected to the female luer connector of the waste fluid passage, the self-venting waste syringe is set to a desired waste blood volume.

It is within the scope of the disclosed method for obtaining a clean blood specimen to obtain multiple blood specimens. After allowing a desired first blood sample into the first blood sample syringe, the flow control member is rotated to close fluid flow from the arterial line. The first blood sample syringe is removed from the female luer connector of the blood sample fluid passage. A self-venting second blood sample syringe is connected to the female luer connector of the blood sample fluid passage. The flow control member is rotated to permit fluid flow between the inlet fluid passage and the blood sample fluid passage and to allow a desired second blood sample into the second blood sample syringe. These steps may be repeated to obtain a desired number of blood samples in additional blood sample syringes.

It should be understood that every maximum numerical limitation given throughout this disclosure is deemed to include each and every lower numerical limitation as an alternative; as if such lower numerical limitations were expressly written herein. Every minimum numerical limitation given throughout this disclosure is deemed to include each and every higher numerical limitation as an alternative, as if such higher numerical limitations were expressly written herein. Every numerical range given throughout this disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is to be understood that both the foregoing general description and the following detailed description are examples and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

DETAILED DESCRIPTION OF THE INVENTION

Figure 1:
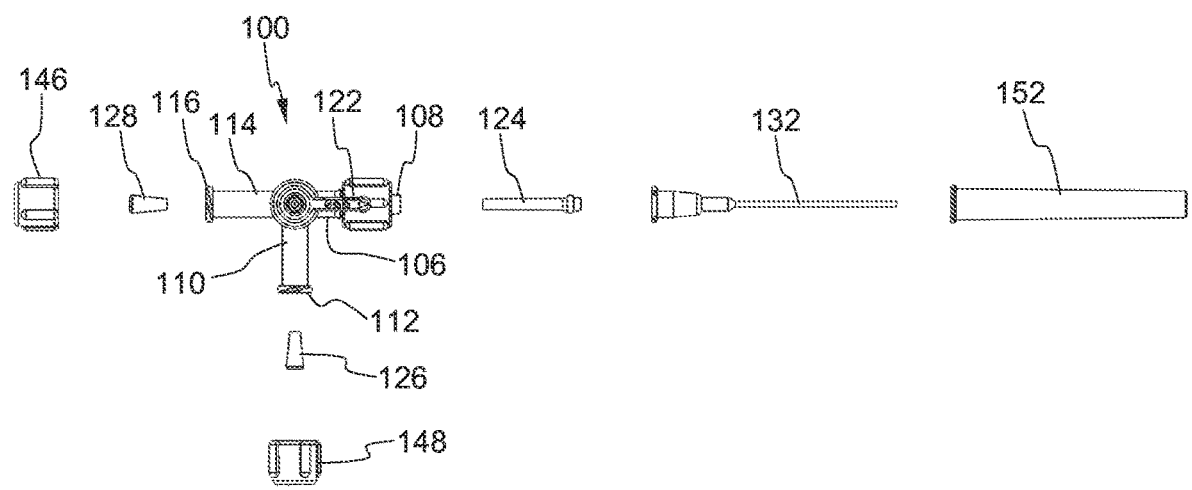
FIG. 1 is an exploded view of a microvolume 3-way stopcock and cannula.
Figure 2:
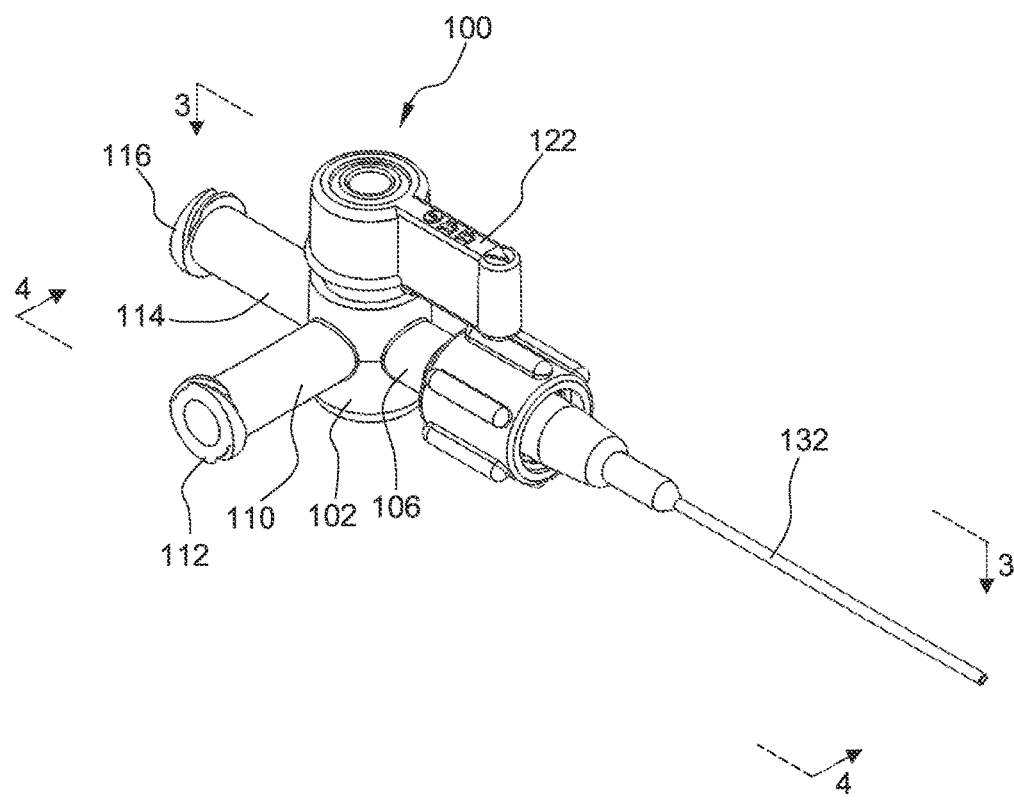
FIG. 2 is an assembled perspective view of the 3-way stopcock and cannula of FIG. 1 with caps removed.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment. Additionally, while the following description refers to several embodiments and examples of the various components and processes of the described invention, all of the described embodiments and examples are to be considered, in all respects, as illustrative only and not as being limiting in any manner.

Furthermore, the described features, structures, characteristics, or methods of the invention may be combined in any suitable manner in one or more embodiments.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the present disclosure generally relate to a blood sampling system and to methods for obtaining a clean blood specimen utilizing the blood sampling system. The disclosed blood sampling system includes a microvolume 3-way stopcock. One example of a microvolume 3-way stopcock 100 is shown in FIGS. 1-4.

The stopcock 100 includes a stopcock body 102. In one or more disclosed embodiments, the stopcock body 102 comprises a cylindrical-shaped central chamber 104, an inlet fluid passage 106 extending from the central chamber to a male luer connector 108, a blood sample fluid passage 110 extending from the central chamber to a female luer connector 112, and a waste fluid passage 114 extending from the central chamber to a female luer connector 116.

Figure 3:
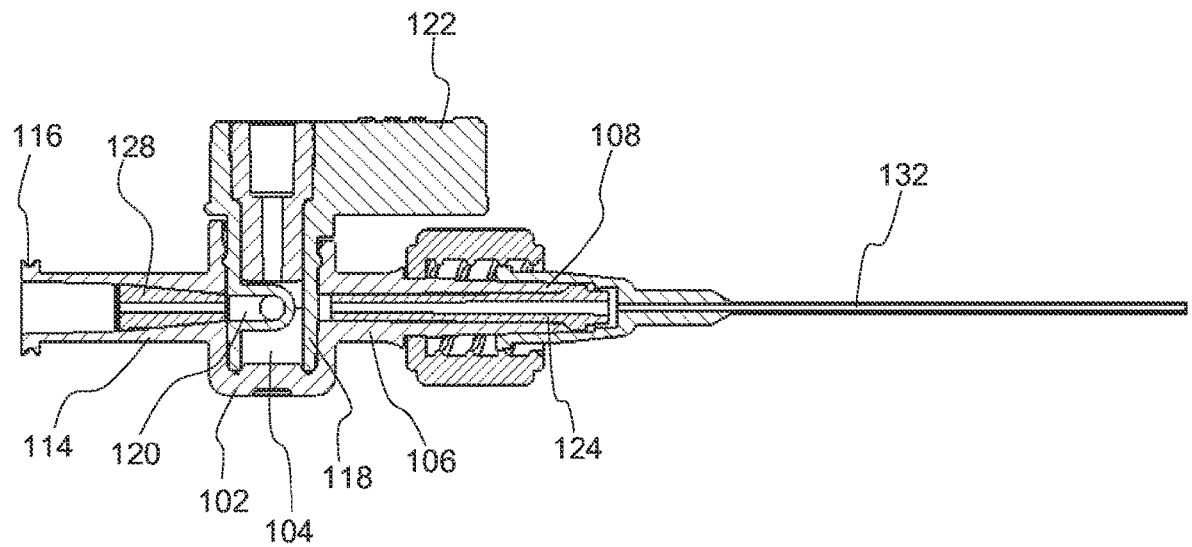
FIG. 3 is a cross-sectional view taken along line 3-3 of FIG. 2.
Figure 4:
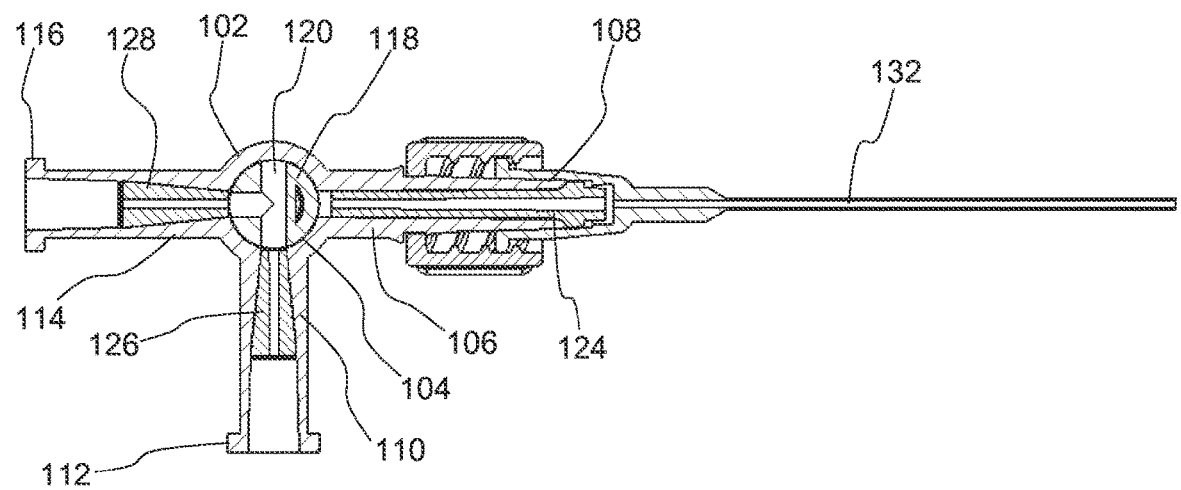
FIG. 4 is a cross-sectional view taken along line 4-4 of FIG. 2.
Figure 5:
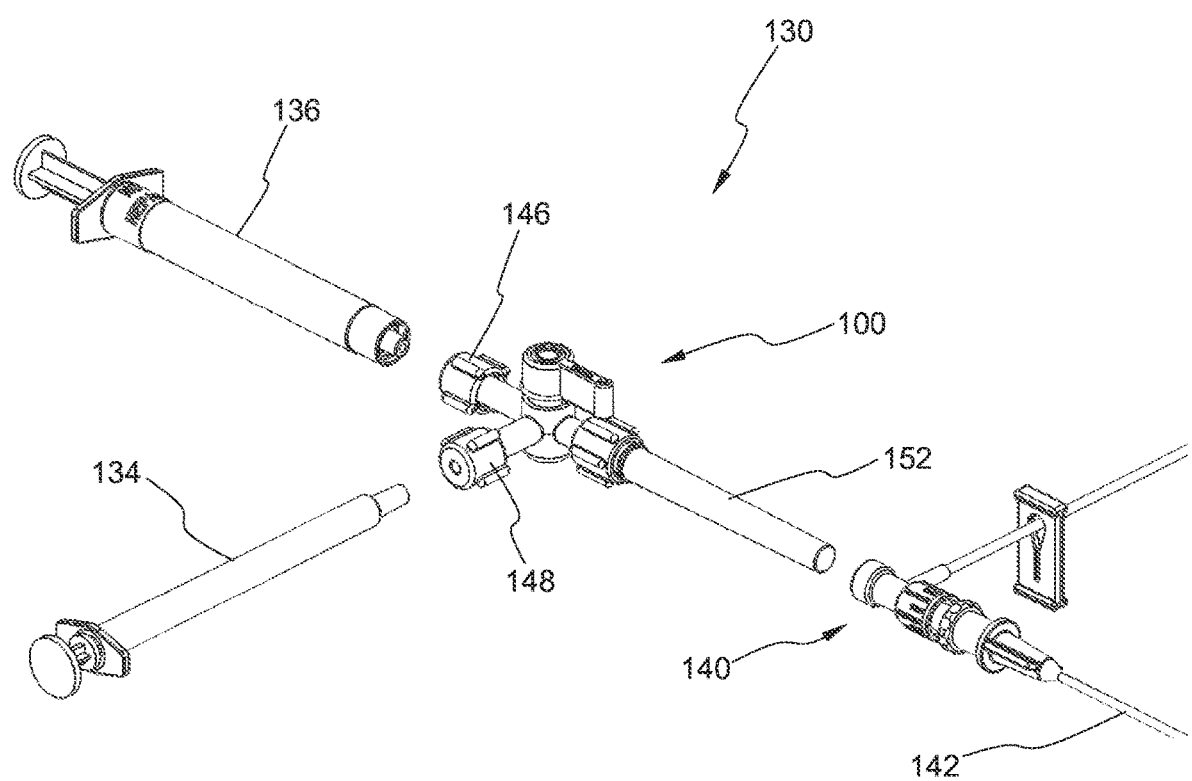
FIG. 5 is a perspective view of a blood sample system containing a microvolume 3-way stopcock.

In one or more disclosed embodiments, a rotatable flow control member 118 is disposed within the central chamber, shown best in FIGS. 3 and 4. The rotatable flow control 118 member may comprise a T-shaped fluid passage 120. The rotatable flow control member provides adjustable fluid communication between the inlet fluid passage 106, the blood sample fluid passage 110, and/or the waste fluid passage 114.

In one or more disclosed embodiments, a lever 122 connected to the rotatable flow control member 118 permits selective rotation of the rotatable flow control member to control fluid flow between the fluid passages 106, 110, and 114.

In one or more disclosed embodiments, the inlet fluid passage 106 comprises a cannula insert 124 disposed within the inlet fluid passage.

In one or more disclosed embodiments, the blood sample fluid passage 110 comprises a blood sample cone 126 disposed within the blood sample fluid passage.

In one or more disclosed embodiments, the waste fluid passage 114 comprises a waste cone 128 disposed within the waste fluid passage.

In one or more disclosed embodiments, the cannula insert 124, the blood sample cone 126, and the waste cone 128 comprise lengthwise fluid pathways having an inner cross-sectional area in the range from 0.3 to 2.0 square millimeters. The cannula insert, blood sample cone, and waste cone serve to fill the inner volume of the fluid passages 106, 110, and 446-114 and thereby reduce the dead space fluid volume of the 3-way stopcock.

In one or more disclosed embodiments, the inlet, blood sample, waste, and T-shaped fluid passages are molded or manufactured to have internal bores with an inner cross-sectional area in the range from 0.3 to 2.0 square millimeters. This embodiment avoids the need for separate cannula insert, blood sample cone, and waste cone structures. The internal bores may have any cross-sectional shape.

In one or more disclosed embodiments, the microvolume 3-way stopcock has a fluid volume dead space in the range of 0.02 to 0.10 mL. In one or more disclosed embodiments, the microvolume 3-way stopcock has a fluid volume dead space in the range of 0.02 to 0.15 mL. In one or more disclosed embodiments, the microvolume 3-way stopcock has a fluid volume dead space in the range of 0.02 to 0.20 mL.

The 3-way stopcock may be implemented in a blood sampling system 130, as shown in FIGS. 5 and 6A-6H. The disclosed blood sampling system may include a cannula with a protective cover 152 connected to the male luer connector 108. The cannula may be any suitable commercially available needle, sharp or blunt, capable of piercing a septum connector to obtain the blood specimen.

The disclosed blood sampling system 130 may further include a self-venting blood sample syringe 134 connected to the female luer connector 112 of the blood sample fluid passage 110. The disclosed blood sampling system 130 may further include a self-venting waste syringe 136 connected to the female luer connector 116 of the waste fluid passage 114. The self-venting syringes 134 and 136 are syringes which automatically evacuate air out of the back of the syringe as the blood fills the syringe during the draw. The self-venting syringes 134 and 136 may have any volume suitable for the desired blood specimen volume. In one non-limiting embodiment, the blood sample syringe 134 has a volume of about 1 mL. In one non-limiting embodiment, the waste syringe 136 has a volume of about 3 mL. The self-venting waste syringe 136 is preferably non-heparinized.

The disclosed blood sampling system 130 may further include a septum connector 140 that attaches directly to the arterial line 142 from which the blood specimen is obtained. Non-limiting examples of an arterial line include an indwelling umbilical arterial catheter (UAC) and a peripheral arterial line (PAL).

The disclosed invention further relates to a method for obtaining a clean blood specimen. In one or more disclosed embodiments of the method, the blood specimen is obtained from an arterial line. In one or more disclosed embodiments of the method, the arterial line is an indwelling umbilical catheter. In one or more disclosed embodiments of the method, the arterial line is a peripheral arterial line.

In the method, a sterile septum connector 140 is connected to the arterial line 142. The sterile septum connector may be connected to the arterial line by a clinician obtaining the blood specimen. If a septum connection is already connected to the arterial line, then the clinician may prepare and sterilize the septum connector. The septum connector provides a closed system access point.

In one or more disclosed embodiments, the method for obtaining a clean blood specimen uses a microvolume 3-way stopcock 100. The 3-way stopcock 100 may comprise an inlet fluid passage 106 having a male luer connector 108, a blood sample fluid passage 110 having a female luer connector, 112 and a waste fluid passage 114 having a female luer connector 116. A cannula 132 may be attached to the male luer connector 108.

In one or more disclosed embodiments, a rotatable flow control member 118 is configured to provide adjustable fluid communication between the inlet fluid passage 106, the blood sample fluid passage 110, and/or the waste fluid passage 114.

In one or more disclosed embodiments, the microvolume 3-way stopcock 100 and cannula 132 have a combined dead space volume in the range from 0.03 to 0.14 mL. In one or more disclosed embodiments, the microvolume 3-way stopcock 100 and cannula 132 have a combined dead space volume in the range from 0.03 to 0.19 mL. In one or more disclosed embodiments, the microvolume 3-way stopcock 100 and cannula 132 have a combined dead space volume in the range from 0.03 to 0.24 mL.

Figure 6A:
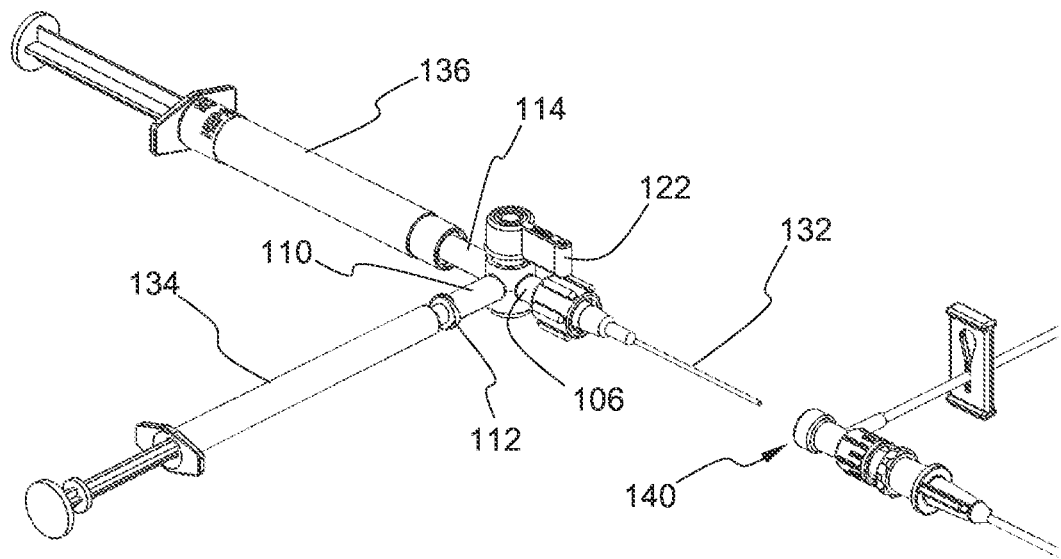
FIGS. 6A-6H are perspective view of various steps of a process for obtaining a blood specimen using a disclosed blood sampling system.

In one or more disclosed embodiments of the method, a self-venting waste syringe 136 is connected to the female luer connector of the waste fluid passage 114, as shown in FIG. 6A. This may be accomplished by removing cap 146 from female luer connector 116 (shown in FIG. 1) and attaching the self-venting waste syringe 136 to the female luer connector 116. In one non-limiting embodiment, the self-venting waste syringe has a volume of about 3 mL. The clinician preferably sets the self-venting waste syringe 136 to a desired volume of waste blood.

In one or more disclosed embodiments of the method, a self-venting blood sample syringe 134 is connected to the blood sample fluid passage 110 as shown in FIG. 6A. This may be accomplished by removing cap 148 from female luer connector 112 and attaching the self-venting blood sample syringe 134 to the female luer connector 112. The clinician preferably sets the self-venting blood sample syringe 134 to a desired blood sample volume.

Figure 6B:
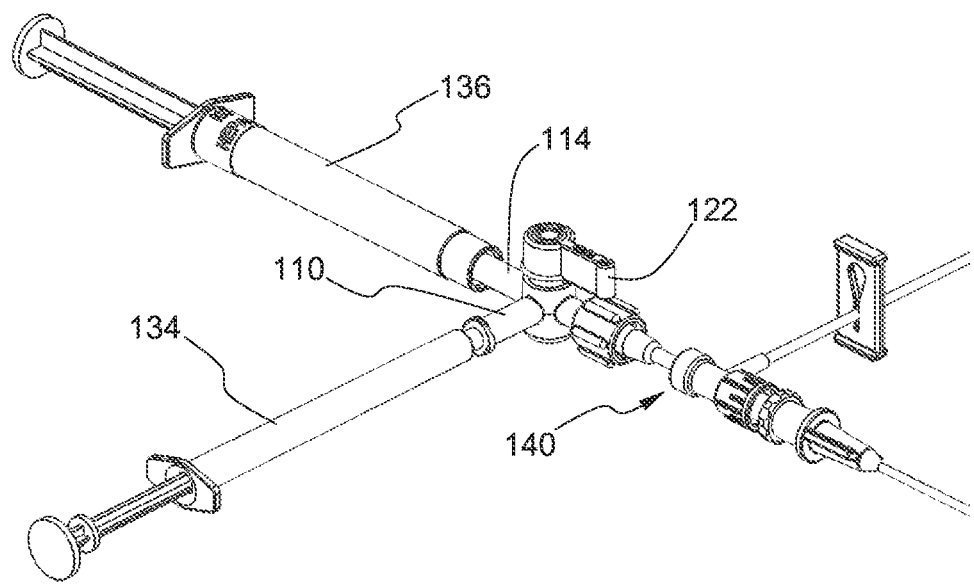

The lever 122 of the flow control member 118 is rotated to close fluid flow from the cannula 132 and the inlet fluid passage 106. As shown in FIGS. 6A-6B, a protective cover 152 (shown in FIG. 5), is removed from the cannula 132. The cannula is slowly and fully inserted perpendicularly into the septum connector 140.

Figure 6C:
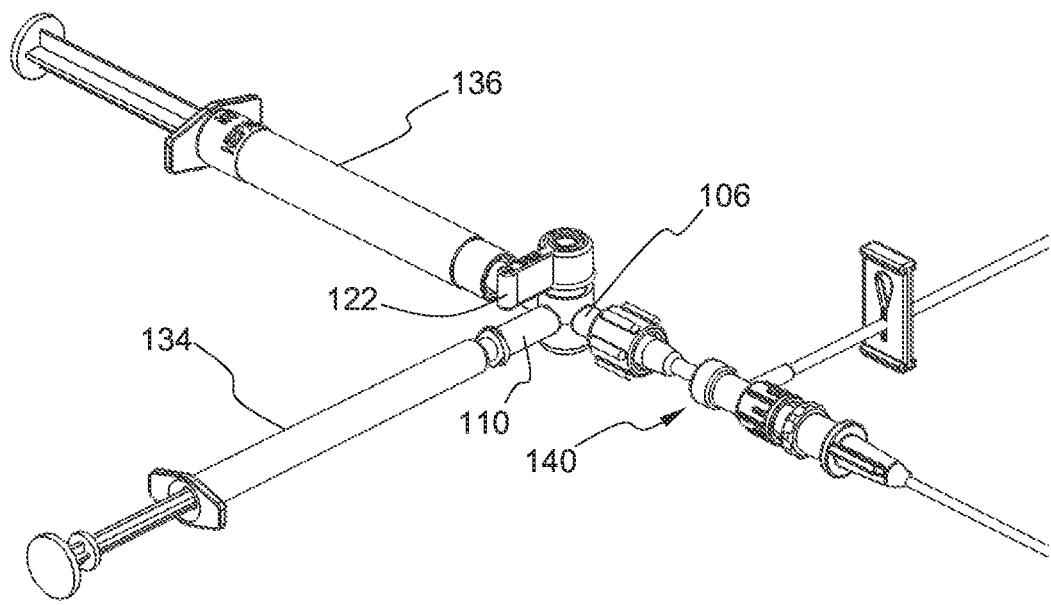

After the cannula is fully inserted, the lever 122 of the flow control member 118 is rotated until it is "OFF" to the blood sample fluid passage 110, to permit fluid flow between the inlet fluid passage 106 and the waste fluid passage 114, thereby allowing the waste fluid to flow freely into the self-venting waste syringe 136, as shown in FIG. 6C. Typically, between 0.5 and 1.0 milliliter of waste blood in the waste syringe 136 is sufficient.

Figure 6D:
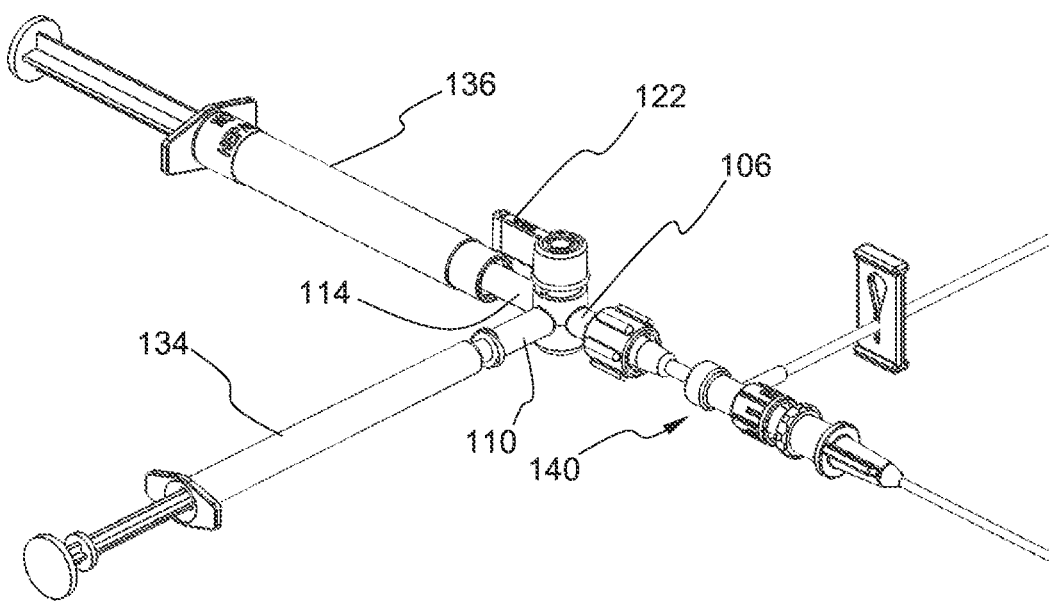

The lever 122 of the flow control member 118 is rotated until it is "OFF" to the waste fluid passage 114, thereby permitting fluid flow between the inlet fluid passage 106 and the blood sample fluid passage 110 and allowing the pure blood sample to flow freely into the blood sample syringe 134, as shown in FIG. 6D.

It is within the scope of the disclosed method to obtain multiple blood specimens. If more than one blood specimen is desired, after the pure blood sample is obtained in the first blood sample syringe 134, then the lever 122 of the flow control member 118 is rotated until it is "OFF" to the blood sample fluid passage 110.

The first blood sample syringe 134 is removed from the female luer connector 112 of the blood sample fluid passage 110. A self-venting second blood sample syringe having the same general configuration as syringe 134 is connected to the female luer connector 112 of the blood sample fluid passage 110 and is set to a desired blood sample volume. The flow control member 118 is rotated to permit fluid flow between the inlet fluid passage 106 and the blood sample fluid passage 110 and to allow a desired second blood sample into the second blood sample syringe. These steps may be repeated to obtain a desired number of blood samples in additional blood sample syringes.

Figure 6E:
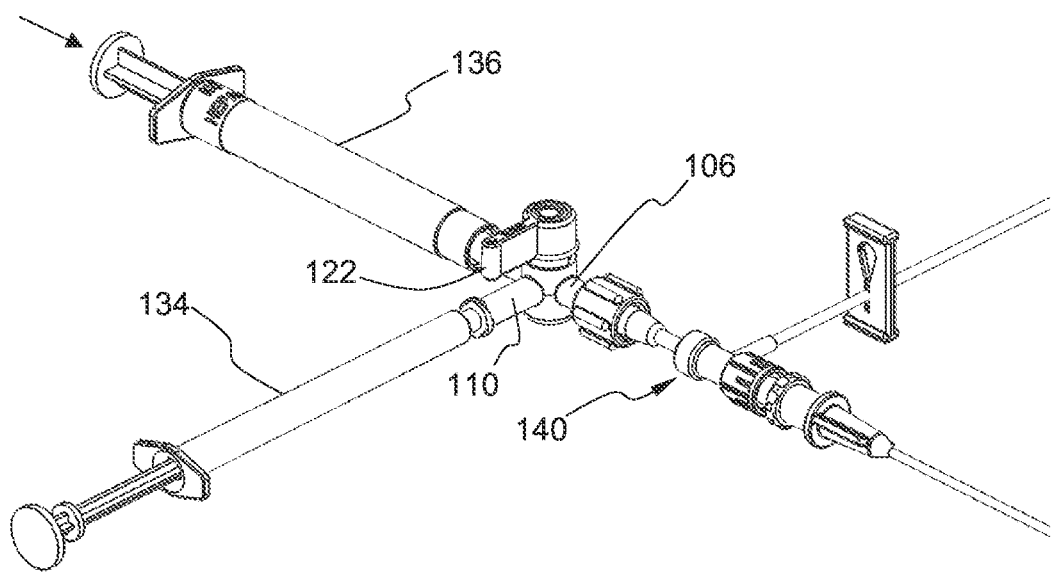

After the desired final volume of pure blood sample is obtained, the lever 122 of the flow control member 118 is rotated until it is "OFF" to the blood sample fluid passage 110, thereby permitting fluid flow between the waste fluid passage 114 and the inlet fluid passage 106. The clinician slowly returns the waste blood within the waste syringe 136 to the patient, as shown in FIG. 6E. A rate of about 2 mL per minute may be used, although this rate may be modified according to medically acceptable guidelines.

Figure 6F:
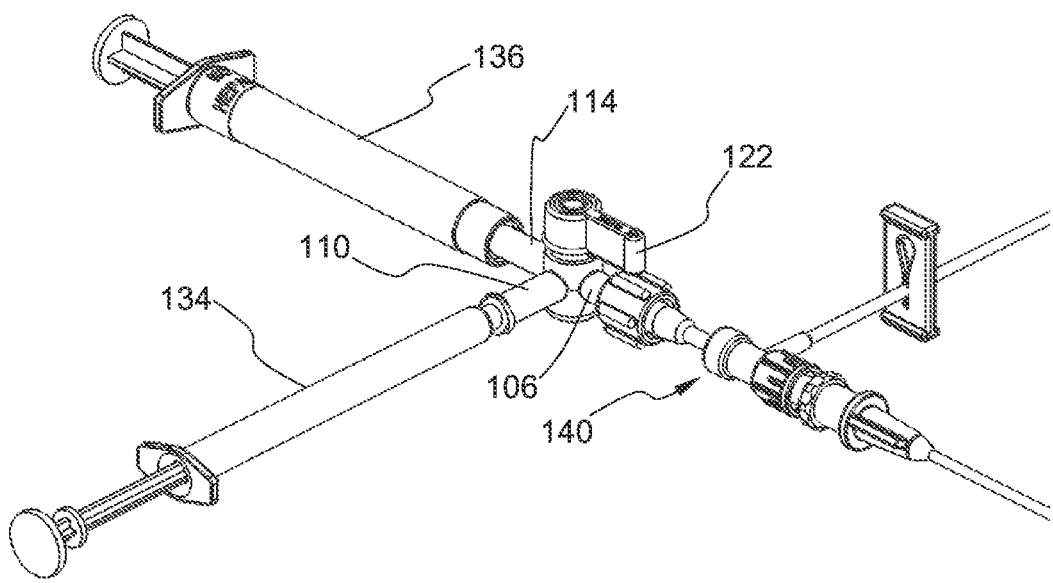
Figure 6G:
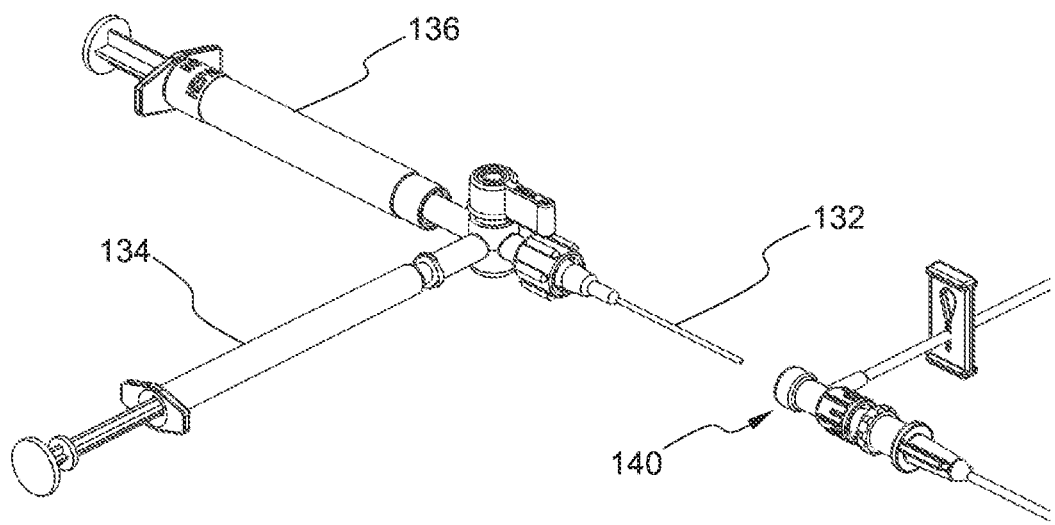
Figure 6H:
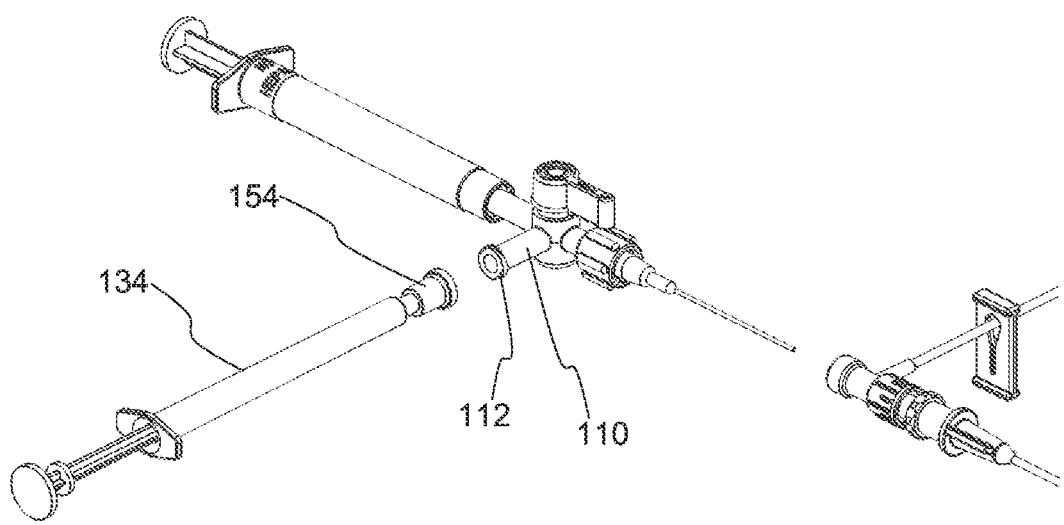

After the waste blood is returned to the patient, the lever 122 of the flow control member 118 is rotated until it is "OFF" to the inlet fluid passage 106, thereby closing fluid flow from the arterial line 142 and the patient, as shown in FIG. 6F. The cannula 132 is removed from the septum connector 140, as shown in FIG. 6G with both the blood sample syringe 134 and waste syringe 136 still attached to the stopcock. The blood sample syringe 134 is removed from the female luer connector 112 of the blood sample fluid passage 110, as shown in FIG. 6H. It is capped for blood sample testing with cap 154.

It will be appreciated that the disclosed blood sampling system includes a microvolume 3-way stopcock having a low dead space fluid volume. The low dead space volume enables the system to be used to safely obtain a blood specimen from neonatal patients having a low total blood volume.

All examples and conditional language recited herein are intended for pedagogical objects to aid the reader in understanding the invention and the concepts contributed by the inventor to furthering the art and are to be construed as being without limitation to such specifically recited examples and conditions. While specific embodiments and examples of the present invention have been illustrated and described, numerous modifications come to mind without significantly departing from the spirit of the invention, and the scope of protection is only limited by the scope of the accompanying claims.

The invention claimed is:

1. A microvolume 3-way stopcock for use in a blood sampling system comprising:
   a stopcock body comprising:
      a cylindrical-shaped central chamber;
      an inlet fluid passage configured to extend from the central chamber to a male luer connector;
      a cannula insert disposed within the inlet fluid passage comprising a lengthwise inlet fluid pathway;
      a blood sample fluid passage configured to extend from the central chamber to a blood sample female luer connector;

a blood sample cone disposed within the blood sample fluid passage comprising a lengthwise blood sample fluid pathway;

a waste fluid passage configured to extend from the central chamber to a waste fluid female luer connector; and a waste cone disposed within the waste fluid passage comprising a lengthwise waste fluid pathway;

a rotatable flow control member disposed within the central chamber and comprising a T-shaped fluid passage, wherein the rotatable flow control member is configured to provide adjustable fluid communication between the inlet fluid passage, the blood sample fluid passage, and/or the waste fluid passage; and a lever connected to the rotatable flow control member configured to permit selective rotation of the rotatable flow control member and control fluid flow between the fluid passages, wherein the inlet fluid pathway, the blood sample fluid pathway, and the waste fluid pathway each have an inner cross-sectional area in the range from 0.3 to 2.0 square millimeters.

2. The microvolume 3-way stopcock for use in a blood sampling system according to claim 1, wherein the microvolume 3-way stopcock has a dead space fluid volume which is an internal fluid volume of the microvolume 3-way stopcock defined by the inlet fluid pathway, the blood sample fluid pathway, the waste fluid pathway, and the T-shaped fluid passage which must be filled with blood before blood can flow into a blood specimen collection device, wherein the microvolume 3-way stopcock has a dead space fluid volume in the range of 0.02 to 0.20 mL.

3. The microvolume 3-way stopcock for use in a blood sampling system according to claim 1, wherein the microvolume 3-way stopcock has a dead space fluid volume which is an internal fluid volume of the microvolume 3-way stopcock defined by the inlet fluid pathway, the blood sample fluid pathway, the waste fluid pathway, and the T-shaped fluid passage which must be filled with blood before blood can flow into a blood specimen collection device, wherein the microvolume 3-way stopcock has a dead space fluid volume in the range of 0.02 to 0.15 mL.

4. The microvolume 3-way stopcock for use in a blood sampling system according to claim 1, wherein the microvolume 3-way stopcock has a dead space fluid volume which is an internal fluid volume of the microvolume 3-way stopcock defined by the inlet fluid pathway, the blood sample fluid pathway, the waste fluid pathway, and the T-shaped fluid passage which must be filled with blood before blood can flow into a blood specimen collection device, wherein the microvolume 3-way stopcock has a dead space fluid volume in the range of 0.02 to 0.10 mL.

5. The microvolume 3-way stopcock for use in a blood sampling system according to claim 1, further comprising a cannula attached to the male luer connector, wherein the microvolume 3-way stopcock and the cannula have a combined dead space fluid volume which is an internal fluid volume of the microvolume 3-way stopcock defined by the inlet fluid pathway, the blood sample fluid pathway, the waste fluid pathway, the T-shaped fluid passage and the cannula which must be filled with blood before blood can flow into a blood specimen collection device, wherein the microvolume 3-way stopcock and the cannula have a combined dead space fluid volume in the rage of 0.03 to 0.24 mL.

6. The microvolume 3-way stopcock for use in a blood sampling system according to claim 1, further comprising a cannula attached to the male luer connector, wherein the microvolume 3-way stopcock and the cannula have a combined dead space fluid volume which is an internal fluid volume of the microvolume 3-way stopcock defined by the inlet fluid pathway, the blood sample fluid pathway, the waste fluid pathway, the T-shaped fluid passage and the cannula which must be filled with blood before blood can flow into a blood specimen collection device, wherein the microvolume 3-way stopcock and the cannula have a combined dead space fluid volume in the rage of 0.03 to 0.19 mL.

7. The microvolume 3-way stopcock for use in a blood sampling system according to claim 1, further comprising a cannula attached to the male luer connector, wherein the microvolume 3-way stopcock and the cannula have a combined dead space fluid volume which is an internal fluid volume of the microvolume 3-way stopcock defined by the inlet fluid pathway, the blood sample fluid pathway, the waste fluid pathway, the T-shaped fluid passage and the cannula which must be filled with blood before blood can flow into a blood specimen collection device, wherein the microvolume 3-way stopcock and the cannula have a combined dead space fluid volume in the rage of 0.03 to 0.14 mL.

8. A blood sampling system comprising:
a microvolume 3-way stopcock according to claim 1;
a cannula connected to the male luer connector;
a self-venting blood sample syringe connected to the blood sample female luer connector of the blood sample fluid passage; and
a self-venting waste syringe connected to the waste fluid female luer connector of the waste fluid passage.

9. The microvolume 3-way stopcock for use in a blood sampling system according to claim 1, wherein T-shaped fluid passage has an inner cross-sectional area in the range from 0.3 to 2.0 square millimeters.

10. A method for obtaining a clean blood specimen comprising:
assuring a sterile septum connector is connected to an arterial line;
obtaining a microvolume 3-way stopcock comprising:
an inlet fluid passage having a male luer connector and a cannula attached to the male luer connector;
a cannula insert disposed within the inlet fluid passage comprising a lengthwise inlet fluid pathway;
a blood sample fluid passage having a blood sample female luer connector;
a blood sample cone disposed within the blood sample fluid passage comprising a lengthwise blood sample fluid pathway;
a waste fluid passage having a waste fluid female luer connector; and
a waste cone disposed within the waste fluid passage comprising a lengthwise waste fluid pathway;
a rotatable flow control member configured to provide adjustable fluid communication between the inlet fluid passage, the blood sample fluid passage, and/or the waste fluid passage,
wherein the microvolume 3-way stopcock and cannula have a combined dead space fluid volume which is an internal fluid volume of the microvolume 3-way stopcock defined by the inlet fluid pathway, the blood sample fluid pathway, the waste fluid pathway, the rotatable flow control member and the cannula which must be filled with blood before blood can flow into a blood specimen collection device, wherein the microvolume 3-way stopcock and the cannula have a combined dead space fluid volume in the range from 0.03 to 0.24 ml;

connecting a self-venting first blood sample syringe to the blood sample female luer connector of the blood sample fluid passage and connecting a self-venting waste syringe to the waste fluid female luer connector of the waste fluid passage;

inserting the cannula into the septum connector;

rotating the flow control member to permit fluid flow between the inlet fluid passage and the waste fluid passage and to allow waste blood into the waste syringe;

rotating the flow control member to permit fluid flow between the inlet fluid passage and the blood sample fluid passage and to allow a desired first blood sample into the first blood sample syringe;

rotating the flow control member to permit fluid flow from the inlet fluid passage and the waste fluid passage; and returning the waste blood from the waste syringe to the patient.

11. The method for obtaining a clean blood specimen according to claim 10, further comprising:

rotating the flow control member to close fluid flow from the arterial line;

removing the cannula from the septum connector; and removing the first blood sample syringe from the blood sample female luer connector of the blood sample fluid passage.

12. The method for obtaining a clean blood specimen according to claim 10, wherein the arterial line comprises an indwelling umbilical catheter.

13. The method for obtaining a clean blood specimen according to claim 10, wherein the arterial line comprises a peripheral arterial line.

14. The method for obtaining a clean blood specimen according to claim 10, wherein after connecting the self-venting first blood sample syringe to the blood sample female luer connector of the blood sample fluid passage, setting the self-venting first blood sample syringe to a desired blood sample volume.

15. The method for obtaining a clean blood specimen according to claim 10, wherein after connecting the self-venting waste syringe to the waste fluid female luer connector of the waste fluid passage, setting the self-venting waste syringe to a desired waste blood volume.

16. The method for obtaining a clean blood specimen according to claim 10, wherein following the step of rotating the flow control member to permit fluid flow between the inlet fluid passage and the blood sample fluid passage and to allow a desired first blood sample into the first blood sample syringe:

rotating the flow control member to close fluid flow from the arterial line;

removing the first blood sample syringe from the blood sample female luer connector of the blood sample fluid passage;

connecting a self-venting second blood sample syringe to the blood sample female luer connector of the blood sample fluid passage; and rotating the flow control member to permit fluid flow between the inlet fluid passage and the blood sample fluid passage and to allow a desired second blood sample into the second blood sample syringe.

17. The method for obtaining a clean blood specimen according to claim 16, wherein following the step of rotating the flow control member to permit fluid flow between the inlet fluid passage and the blood sample fluid passage and to allow a desired second blood sample into the second blood sample syringe:

rotating the flow control member to close fluid flow from the arterial line;

removing the second blood sample syringe from the blood sample female luer connector of the blood sample fluid passage;

connecting a self-venting third blood sample syringe to the blood sample female luer connector of the blood sample fluid passage; and rotating the flow control member to permit fluid flow between the inlet fluid passage and the blood sample fluid passage and to allow a desired third blood sample into the third blood sample syringe.

18. The method for obtaining a clean blood specimen according to claim 10, wherein the microvolume 3-way stopcock and the cannula have a combined dead space fluid volume in the range from 0.03 to 0.19 mL.

19. The method for obtaining a clean blood specimen according to claim 10, wherein the microvolume 3-way stopcock and the cannula have a combined dead space fluid volume in the range from 0.03 to 0.14 mL.

* * * * *